(12) United States Patent
Wang et al.

(10) Patent No.: US 12,275,138 B2
(45) Date of Patent: Apr. 15, 2025

(54) CONNECTING MECHANISM

(71) Applicant: Shenzhen Edge Medical CO.,Ltd., Shenzhen (CN)

(72) Inventors: Jianchen Wang, Shenzhen (CN); Yuanqian Gao, Shenzhen (CN)

(73) Assignee: Shenzhen Edge Medical CO., Ltd., Guangdong (CN)

( * ) Notice: Subject to any disclaimer, the term of this patent is extended or adjusted under 35 U.S.C. 154(b) by 964 days.

(21) Appl. No.: 17/110,006

(22) Filed: Dec. 2, 2020

(65) Prior Publication Data
US 2021/0085300 A1     Mar. 25, 2021

Related U.S. Application Data

(63) Continuation of application No. PCT/CN2019/092419, filed on Jun. 21, 2019.

(30) Foreign Application Priority Data

Jun. 22, 2018 (CN) .......................... 201810650764.3

(51) Int. Cl.
*B25J 15/04* (2006.01)
*A61B 17/00* (2006.01)

(52) U.S. Cl.
CPC . *B25J 15/0408* (2013.01); *A61B 2017/00477* (2013.01)

(58) Field of Classification Search
CPC .......... A61B 17/00; A61B 2017/00477; A61B 34/30; A61B 34/37; B25J 15/04;
(Continued)

(56) References Cited

U.S. PATENT DOCUMENTS 7,883,423 B2 * 2/2011 Kubota ...................... F16D 3/68
  464/73
8,814,710 B2 * 8/2014 Zhao ........................ F16D 3/68
  464/157
(Continued)

FOREIGN PATENT DOCUMENTS

| CN | 102630154 A | 8/2012 | |
| CN | 105636543 A | 6/2016 | |
| WO | WO-2011037394 A2 * | 3/2011 | ............. A61B 17/00 |

OTHER PUBLICATIONS

WO 2011037394 A2 (Jae Sun Lee) Mar. 31, 2011. [online] [retrieved on Feb. 6, 2024]. Retrieved from: Clarivate Analytics. (Year: 2011 ).*

*Primary Examiner* — Joseph Brown
(74) *Attorney, Agent, or Firm* — ScienBiziP, P.C.

(57) ABSTRACT

The application discloses a connecting mechanism, a power mechanism, an operating am, and a slave operating device. The connecting mechanism includes a main body and a connecting unit. The main body includes a first mounting wall and a second mounting wall for abutting against the operating arm and the power mechanism respectively. The connecting unit is disposed on the main body. The connecting unit includes a first connecting coupler and a second connecting coupler. The first and second connecting couplers are configured to abut against a power connecting coupler and a driven connecting coupler respectively, thereby enabling the power mechanism to drive the operating arm via the connecting unit. At least one of the first connecting coupler and the power connecting coupler is movable along a first abutting direction, and at least one of the second connecting coupler and the driven connecting coupler is movable along a second abutting direction.

18 Claims, 7 Drawing Sheets

(58) Field of Classification Search
CPC .......................... B25J 15/0408; B25J 15/0458; B25J 19/0025; B25J 19/0029; B25J 19/0033; B25J 19/0041
USPC .......................................................... 464/73
See application file for complete search history.

(56) References Cited

U.S. PATENT DOCUMENTS

| | | | |
|---|---|---|---|
| 2003/0050122 A1* | 3/2003 | Yorston ..................... | F16D 1/12 464/73 |
| 2015/0298733 A1* | 10/2015 | Moriyama ............. | B62D 7/224 180/444 |
| 2018/0116738 A1* | 5/2018 | Bajo ................... | H02K 7/1163 |
| 2018/0168752 A1 | 6/2018 | Scheib et al. | |

\* cited by examiner

CONNECTING MECHANISM

FIELD

The subject matter herein generally relates to minimally invasive surgeries, in particular to a connecting mechanism.

BACKGROUND

Minimally invasive surgery refers to a surgical method for performing a procedure in a human body cavity using modern medical instruments and related devices such as laparoscopes, thoracoscopes, and the like. Compared with the traditional surgery mode, the minimally invasive surgery has the advantages of being small in trauma, light in pain, fast in recovery and the like.

With advances in science and technology, minimally invasive surgical robot technologies are increasingly mature and widely used. A minimally invasive surgical robot typically includes a master console and a slave operating device. The master console is used for sending control commands to control the slave operating device for performing the corresponding operation according to the surgeon's operation.

The slave operating device typically includes a power mechanism, a connecting mechanism, and an operating arm connected to each other in sequence. The power mechanism drives the operating arm via the connecting mechanism. The operating arm is used for extending into the body to perform a surgical operation. At present, when the power mechanism drives the operating arm via the connecting mechanism, the error is large, thereby enabling the control accuracy and operation accuracy of the operating arm to be poor.

SUMMARY

In view of the above problems, the present disclosure provides a connecting mechanism for enabling the operating arm connected to the connecting mechanism to have better control and operation accuracy.

A connecting mechanism, includes:
  a main body, including a first mounting wall and a second mounting wall for abutting against an operating arm and a power mechanism respectively;
  a connecting unit, disposed on the main body, the connecting unit including a first connecting coupler and a second connecting coupler, the first connecting coupler configured to abut against the power connecting coupler of the power mechanism along a first abutting direction, and the second connecting coupler configured to abut against the driven connecting coupler of the operating arm along a second abutting direction, thereby enabling the power mechanism to drive the operating arm by the connecting unit, at least one of the first connecting coupler and the power connecting coupler being movable along the first abutting direction, at least one of the second connecting coupler and the driven connecting coupler being movable along the second abutting direction.

At least one of the connecting couplers, abutting against each other, is capable of moving relative to the main body when the connecting mechanism having the above described connecting unit is connected to the corresponding operating arm and the power mechanism, thereby reducing the mounting gap and the driving error, and enabling the operation and the control of the operating arm to be more precise.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings and following descriptions show merely some embodiments of the present invention, and a person of ordinary skill in the art may still derive other drawings from these accompanying drawings without creative efforts.

DETAILED DESCRIPTION

Figure 1:
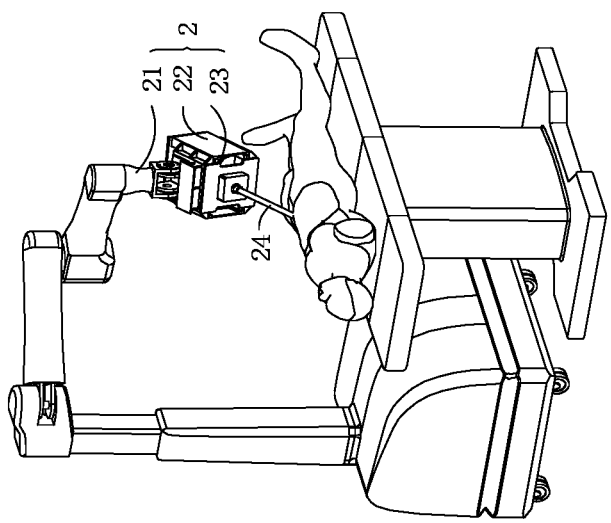
FIG. 1 is a structural schematic view of an embodiment of a surgical robot according to the present disclosure.
Figure 1:
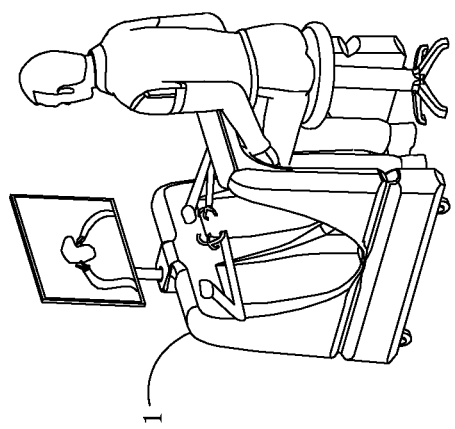

Implementations of the disclosure will now be described, by way of embodiments only, with reference to the drawing. The disclosure is illustrative only, and changes may be made in the detail within the principles of the present disclosure. It will, therefore, be appreciated that the embodiments may be modified within the scope of the claims.

For ease of understanding of the present application, the present application will be described more fully hereinafter with reference to the associated drawings. Preferred embodiments of the present application are set forth in the accompanying drawings. This application may, however, be embodied in many different forms and is not limited to the embodiments described herein. Rather, these embodiments are provided for the purpose of providing a more thorough and thorough understanding of the disclosure of the present application.

It should be noted that when an element is referred to as being "disposed on" another element, it may be directly on the other element or intervening elements may also be present. When an element is considered to be "connected" to another element, it may be directly connected to another element or intervening elements may be present at the same time. When an element is considered to be "coupled" to another element, it may be directly coupled to another element or intervening elements may be present at the same time. As used herein, the terms "vertical", "horizontal", "left", "right" and the like are intended for purposes of illustration only and are not intended to be limiting. As used herein, the terms "distal end" and "proximal end" are common terms in the art of interventional medical devices, where "distal end" refers to the end far away from the operator during the surgical procedure, and the "proximal end" refers to the end close to the operator during the surgical procedure.

Unless defined otherwise, all technical and scientific terms used herein have the same meaning as commonly understood by one of ordinary skill in the art. The terminology used herein is for the purpose of describing particular embodiments only and is not intended to be limiting of the invention. As used herein, the term "and/or" includes any and all combinations of one or more of the associated listed items.

Figure 2:
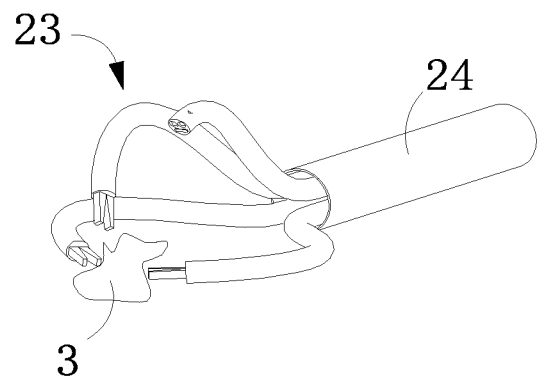
FIGS. 2 and 3 are partial schematic views of different embodiments of a slave operating device according to the present disclosure.
Figure 3:
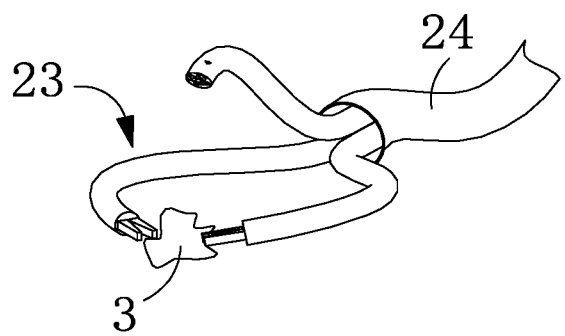

As shown in FIGS. 1-3, a surgical robot includes a master console 1 and a slave operating device 2. Wherein the master console 1 is used for sending control commands to the slave operating device 2 according to the operation of the surgeon to control the slave operating device 2. The master console 1 is also used for displaying images acquired from the slave operating device 2. The slave operating device 2 is used for responding to the control commands sent by the master console 1 and performing corresponding operations, and the slave operating device 2 is also used for acquiring images in the human body.

Specifically, the slave operating device 2 includes a mechanical arm 21, a power mechanism 22 disposed on the mechanical arm 21, an operating arm 23 disposed on the power mechanism 22, and a sleeve 24 sleeving the operating arm 23. The mechanical arm 21 is used for adjusting the position of the operating arm 23. The power mechanism 22 is used for driving the operating arm 23 to perform a corresponding operation. The operating arm 23 is used for extending into the human body and performing a surgical operation by the end effector 20 located at the distal end of the operating arm, and/or acquiring images within the human body. Specifically, as shown in FIG. 2 and FIG. 3, the operating arm 23 passes through the sleeve 24, and the end effector extends out of the sleeve 4 and is driven by the power mechanism 22 to perform the operation. In FIG. 2, the part of the operating arm 23 located in the sleeve 24 is a rigid part. In FIG. 3, the part of the operating arm 23 located in the sleeve 24 is a flexible part, and the sleeve bends with the flexible region. In another embodiment, the sleeve 24 may also be omitted, at which point the sleeve is not required.

In one embodiment, there is a plurality of operating arms 23 disposed on the same power mechanism 22, and the distal ends of the plurality of operating arms 23 extend into the human body via an incision in the human body to move the end effectors 20 of the operating arm 23 to the vicinity of the lesion 3 for a surgical operation. Specifically, the power mechanism has a plurality of power portions, and each power portion 22 is connected to an operating arm. In another embodiment, the power mechanism has a plurality of power mechanisms 22 and each power mechanism 2 is connected to an operating arm 23. In another embodiment, the power mechanism is a plurality of power mechanisms 22. Each power mechanism 22 is provided with an operating arm 23, and the plurality of operating arms extend into the human body via one incision, and the plurality of power mechanisms 22 may be disposed on a mechanical arm 21 or on a plurality of mechanical arms 21. It should be noted that the plurality of operating arms 23 may also extend into the human body via a plurality of incisions. For example, there are two operating arms extending into each of the incisions, or there is one operating arm extending into each of the incisions.

In one embodiment, the slave operating device 2 further includes a trocar for penetrating the incision in the human body and fixedly disposed in the trocar, and the operating arm extends into the body via the trocar.

Figure 4:
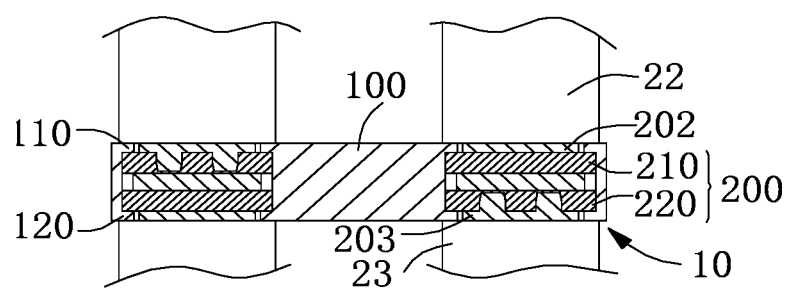
FIG. 4 is a partial cross-sectional view of an embodiment of a connecting mechanism according to the present disclosure.

As shown in FIG. 4, the slave operating device 2 further includes a connecting mechanism 10 for connecting between the power mechanism 22 and the operating arm 23, thereby enabling the power mechanism 22 to drive the operating arm 23. The connecting mechanism 10 includes a main body 100 and a connecting unit 200. Wherein the connecting unit 200 is rotatably mounted to the main body 100 and is connected to the driven connecting coupler 203 of the operating arm 23 and the power connecting coupler 202 of the power mechanism 22, thereby enabling the power mechanism 22 to drive the driven connecting coupler 203 of the operating arm 23 to rotate to drive the operating arm 23 to perform the corresponding operation by driving the connecting unit 200 to rotate. It should be noted that the power mechanism is capable of moving along a driving direction and does not need to be rotatably disposed on the main body when the power mechanism is in a linear driving model instead of a rotational driving model. The power mechanism is adjusted by the embodiments described below.

Figure 5:
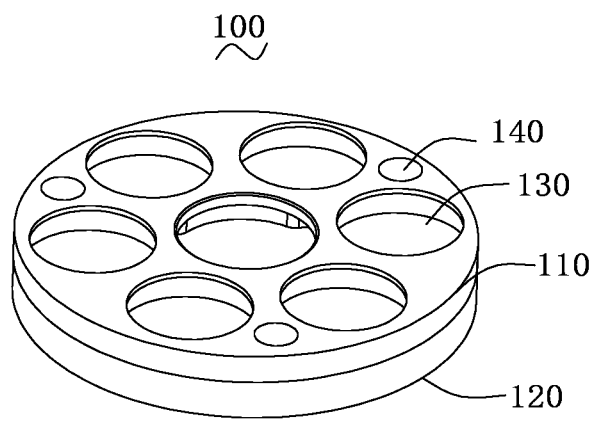
FIG. 5 is a structural schematic view of different embodiments of a connecting mechanism according to the present disclosure.

As shown in FIG. 5, the main body includes a first mounting wall 110, a second mounting wall 120 for abutting against the power mechanism 22 and the operating arm 23 respectively. In one embodiment, the main body 100 defines a mounting slot 130, passing through the first mounting wall 110 and the second mounting wall 120, for receiving the connecting unit 200. There is a plurality of mounting slot 130 and the plurality of the mounting slots 130 is placed around the main body 100. At this time, the power mechanism includes a plurality of power couplers 202 for driving the corresponding driven connecting coupler 203. In another embodiment, the mounting slots 130 are arranged in another way. For example, the mounting slots 130 are arranged linearly. Or there is only one mounting slot 130.

In one embodiment, there is a positioning unit 140 mounted on the main body 100 for positioning the operating arm 23 and/or the power mechanism 22. That is the positioning unit 140 positions the operating arm 23 and/or power mechanism 22 when the positioning unit 140 is connected to the operating arm 23 and/or power mechanism 22. Specifically, the positioning unit 140 is three positioning holes arranged in a triangle. Wherein the positioning hole is a through hole or blind hole. In another embodiment, the positioning unit 140 may be another structure, such as a positioning post. In addition, the positioning unit 140 may also be omitted, at which point the positioning unit 140 is not needed.

In one embodiment, there is a mounting unit (not shown) mounted to the main body 100 for securing the operating arm 23 and/or the power mechanism 22. For example, the mounting unit is an engaging structure and engages with the operating arm 23 and the power mechanism 22, thereby enable the power mechanism 22 and the operating arm 23 to be secured to the main body 100. As another example, the mounting unit is a threaded fastening structure which is screwed with the power mechanism 22, and as another example, the mounting unit is an electromagnet assembly to be magnetically connected to the power mechanism 22 and the operating arm 23.

Please referring to FIGS. 6 to 10, in one embodiment, the connecting unit 200 includes a first connecting coupler 210, a second connecting coupler 220. The first connecting coupler 210 is used for abutting against the power connecting coupler 202 of the power mechanism 22 along a first abutting direction. The second connecting coupler 220 is used for abutting against the driven connecting coupler 203 of the operating arm 23 along a second abutting direction, to enable the power mechanism 22 to drive the operating arm 23 by the connecting unit 200. Wherein at least one of the first connecting coupler 210 and the power connecting coupler 202 is capable of moving along the first abutting direction, and at least one of the second connecting coupler 220 and the driven connecting coupler 203 is capable of moving along the second abutting direction, thereby reducing a mounting gap between the connecting unit 200 and the operating arm 220 or the power mechanism 22. For example, the first connecting coupler 210, the second connecting coupler 220 is capable of moving along the abutting direction relative to the main body 100. As another example, the first connecting 210 and the driven connecting coupler 203 is capable of moving along the abutting direction relative to the main body 100. And as another example, the power connecting coupler 202, the second connecting coupler 220 is capable of moving along the abutting direction relative to the main body 100. As another example, the first connecting coupler and the second connecting coupler is not capable of moving along the abutting direction, and the power connecting coupler and the driven connecting coupler is capable of moving along the abutting direction. Wherein being capable of moving along the abutting direction is that the connecting coupler is capable of moving along the abutting direction when the main body 100 of the connecting mechanism 10 abuts against or is close to abut against the operating arm 23 and/or the power mechanism 22. When the main body 100 is substantially stationary relative to the operating arm 23 and/or the power mechanism 22, the connecting mechanism 10 is moved by the connecting coupler to reduce the mounting gap. The connecting coupler includes a first connecting coupler 210, a second connecting coupler 220, a driving connecting coupler 203 and a power connecting coupler 202.

One of the connecting couplers abutting against each other is capable of moving relative to the main body 100 when the connecting mechanism having the above described connecting unit 200 is connected to the corresponding operating arm 23 and the power mechanism 22, thereby reducing the mounting gap and the driving error, and enabling the operation and the control of the operating arm 23 to be more precise.

In one embodiment, the first connecting coupler 210 and the second connecting coupler 220 are capable of moving along the abutting direction relative to the main body 100, and the first connecting coupler 210 and the second connecting coupler 220 are arranged opposite to each other. In one embodiment shown in FIGS. 4, 6, 8, and 9, the edge areas of the first connecting coupler 210 and the second connecting coupler 220 and abut against inner surfaces of the first mounting wall 110 and the second mounting wall 120 respectively, thereby enabling the connecting unit 200 to be received in the mounting slot 130 and to limit the movement of the first mounting wall 110 and the second mounting wall 120. In another embodiment, one end of the connecting unit 200 may also extend out of the mounting slot 130 and another end of the connecting unit 200 is located in the mounting slot 130.

In one embodiment shown in FIGS. 6 to 9, the rotation axes of the first connecting coupler 210 and the second connecting coupler 220 of the connecting unit 200 overlap. In another embodiment, the rotation axes of the first connecting coupler 210 and the second connecting coupler 220 also form an acute angle or a right angle, i.e., the rotation axes of the first connecting coupler and the second connecting coupler form an acute angle or a straight angle. At this time, the connecting unit 200 is a bent structure, and the two connecting couplers are at an acute angle or a right angle, and the first connecting coupler 210 is connected to the second connecting coupler 220 by a driven unit, thereby enabling the first connecting coupler 210 and the second connecting coupler 220 to rotate synchronously.

Figure 8:
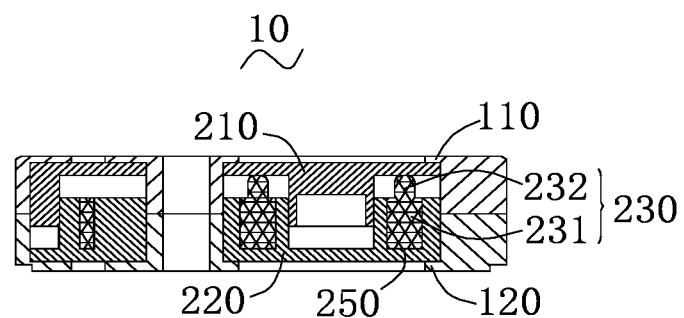

As shown in FIG. 8, in one embodiment, the first connecting coupler 210 and the second connecting coupler 220 of the connecting unit 200 move relative to the main body 100 respectively, that is, when the first connecting coupler 210 moves, the state of the second connecting coupler 220 is not affected, and vice versa. Specifically, the connecting unit 200 further includes an elastic unit 230, the two ends of the elastic unit 230 respectively abut against the first connecting coupler 210 and the second connecting coupler 220, so that the edge areas of the two connecting couplers abut against the inner surface of the first mounting wall 110 and the second mounting wall 120, i.e., when the operating arm 23 and the power mechanism 22 are not connected, the elastic unit 230 is in a compressed state to ensure that the first connecting coupler 210 and the second connecting coupler 220 abut against the two mounting walls. In another embodiment, the elastic unit 230 may also be omitted, at which time an elastic connecting coupler may be used instead.

Figure 9:
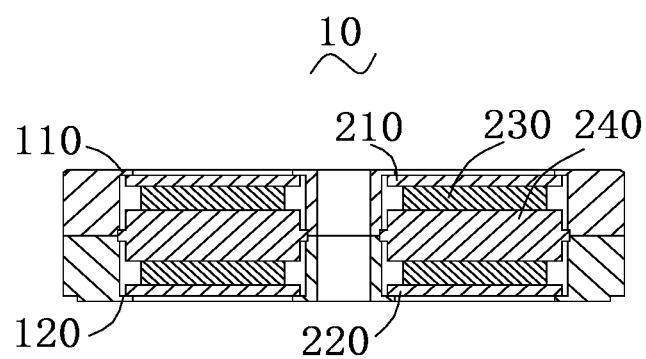

In another embodiment, the connecting unit 200 may be another structure to enable the two connecting couplers to move independently. As shown in FIG. 9, in one embodiment, the connecting unit 200 further includes a main body portion 240, a first connecting coupler 210, and a second connecting coupler 220 connected to the main body portion 240 by the elastic unit 230. Specifically, the main body portion 240 is rotatably mounted to the main body 100, and both sides of the main body portion 240 are provided with elastic units 230. Another side of the elastic unit 230 is connected to the first connecting coupler 210 or the second connecting coupler 220, and the main body portion 240 is not movable along the abutting direction so as to enable the two connecting couplers, connected to the main body 240, to move independently. At this time, the elastic unit 230 only abuts against the first connecting coupler 210 or the second connecting coupler 220, thereby enabling the first connecting coupler 210 to abut against the power connecting coupler 202, or enabling the second connecting coupler 220 to abut against the driven connecting coupler 203.

In another embodiment, the first connecting coupler 210 and the second connecting coupler 220 of the connecting unit 200 may also move synchronously relative to the main body 100. At this time, the driven connecting coupler 203 and/or the power connecting coupler 202 is also capable of moving along the abutting direction, and the elastic units 230 are arranged on the driven connecting coupler 203 and/or the power connecting coupler 202, thereby enabling the corresponding connecting couplers to abut against each other. For example, the connecting unit includes an elastic unit so that the elastic unit abuts against the power connecting coupler through the first connecting coupler, and at the moment, an elastic unit is also arranged on the driven connecting coupler so as to abut against the second connecting coupler when the elastic unit is connected to the connecting mechanism 10.

The elastic unit 230 of the connecting unit 200 may be one of a variety of structures. As shown in FIG. 8, the elastic unit 230 includes a first connecting post 231 and a second connecting post 232. The first connecting post 231 and the second connecting post 232 are elastically connected. The first connecting post 231 and the second connecting post 232 are configured to abut against two connecting couplers which are oppositely arranged. The second connecting coupler 220 defines a receiving hole 250 for receiving the first connecting post 231. The first connecting post 231 is received in the receiving hole 250, and abuts against the bottom surface of the receiving hole 250, thereby enabling the elastic unit 230 to be more stably connected to the second connecting coupler 220, and enabling the second connecting post 232 to abut against the first connecting coupler 210. In another embodiment, the receiving hole is defined in the first connecting coupler 210, or each of the first connecting coupler 210 and the second connecting coupler 220 defines a receiving hole. The receiving hole is configured to receive the first connecting post 231 or the second connecting post 232. For example, the first connecting coupler 210 defines a receiving hole, one end of the first connecting post 231 or the second connecting post 232 is received in the receiving hole, and the other end of the first connecting post 231 or the second connecting post 232 abuts against the second connecting coupler 220. As another example, each of the first connecting coupler 210 and the second connecting coupler 220 defines a receiving hole for receiving the first connecting post 231. At this point, the first connecting posts 231 of a part of the connecting units 200 are received in the receiving holes of the first connecting coupler 210. The second connecting posts 232 abut against the second connecting coupler 220. The first connecting post 231 of the partial connecting unit 200 is received in the receiving hole of the second connecting coupler 220. The second connecting post 232 abuts against the first connecting coupler 210. For example, the first connecting coupler 210 defines a receiving hole for receiving the first connecting post 231 and the second connecting post 232. The first connecting posts 231 of a part of the elastic units 230 are received in the connecting hole. The second connecting post 232 abuts against the second connecting coupler 220. The first connecting post 231 of a part of the elastic unit 230 abuts against the second connecting coupler 220, and the second connecting post 232 is received in the receiving hole. In another embodiment, the receiving holes may also be omitted. Alternatively, the elastic unit 230 may be another structure. For example, the elastic unit 230 is a spring.

Figure 6:
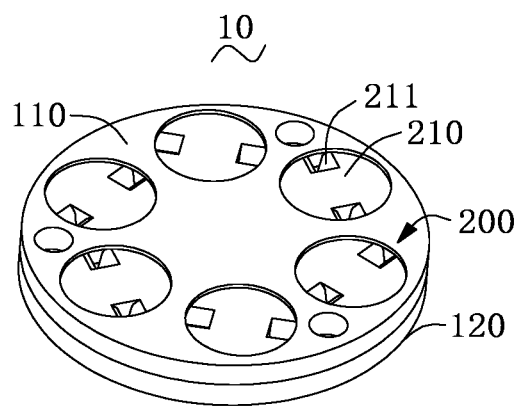
FIGS. 6 to 9 are structural schematic views of different embodiments of a connecting mechanism according to the present disclosure.
Figure 7:
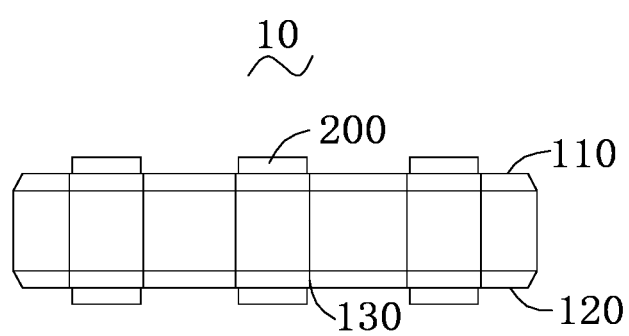
Figure 10:
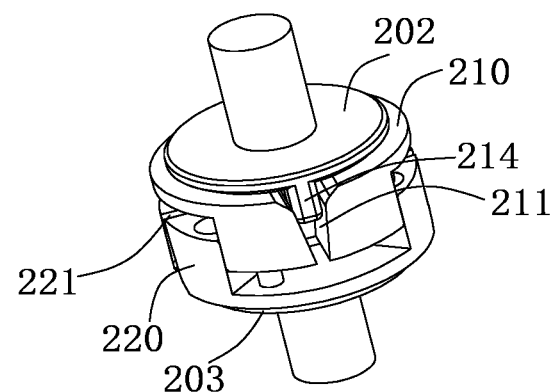
FIGS. 10 and 11 are structural schematic views of different viewing angles of a connecting unit and a power connecting coupler, and a driven connecting coupler according to an embodiment of the present disclosure.
Figure 11:
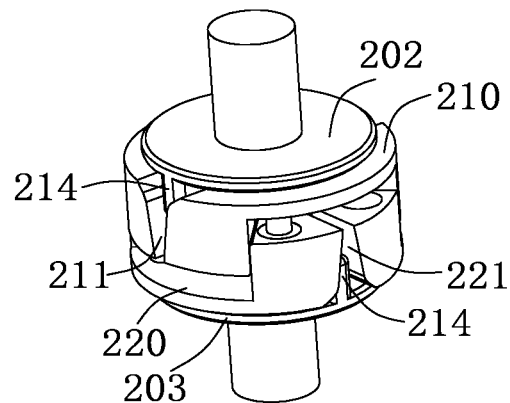

As shown in FIG. 6, the first connecting coupler 210 defines a first mounting part 211, and the second connecting coupler 220 defines a second mounting part 221. The first mounting part and the second mounting part are configured to be connected to the corresponding structures of the power connecting coupler 202 of the power mechanism and the driven connecting coupler 203 of the operating arm respectively. FIG. 10 and FIG. 11 are structural schematic views of different viewing angles of the connecting unit, the power connecting coupler, and the driven connecting coupler. In one embodiment, the first mounting part 211 and the second mounting part 221 are hole structures, and at this point, the power connecting coupler 202 and the driven connecting coupler 203 have mounting posts 214 corresponding to the hole structures, thereby connecting to the corresponding mounting parts. In another embodiment, only one of the two mounting parts may be a hole structure. The first mounting part 211 or the second mounting part 221 may be a through hole or a blind hole. For example, the two mounting parts are blind holes, and the power connecting coupler 202 and the driven connecting coupler 203 both have mounting posts and are received in the corresponding hole respectively. It should be noted that, in one embodiment, the first mounting part 211 and/or the second mounting part 221 are tapered holes, thereby further reducing the mounting gap between the plurality of connecting couplers. In one embodiment, the mounting post 214 may be a tapered post structure to further reduce the mounting gap between the plurality of connecting couplers. The free end of the post structure may also have a rounded corner structure. For example, the corner is connected to the inner wall of the mounting part to form a line contact.

In addition, as shown in FIG. 10 and FIG. 11, after the power connecting coupler 202 is connected to the first connecting coupler 210, the mounting post 214 and the first mounting part 211 form a self-locking structure. Specifically, the inner wall of the first mounting part 211 forms an included angle with the mounting post 214 of the power connecting coupler 202, thereby enabling the mounting post 214 to be locked with the first mounting part 211. The mounting post 214 and the second mounting part 221 form a self-locking structure, i.e., the inner wall of the second mounting part 221 forms an included angle with the connecting post of the driven connecting coupler 203. In one embodiment, the included angle is 2-30 degrees, such as 8 degrees. The included angle may be another value.

In another embodiment, the first mounting part 211 and/or the second mounting part 221 may also be a post structure, at this point, the corresponding connecting coupler includes a hole structure, for connecting to the corresponding mounting part. The hole structure is the same as that of the embodiments described above, and is not repeated here.

It should be noted that when the mounting part or the mounting structure corresponding to the mounting part is a post structure, the post structure may include a first connecting portion and a second connecting portion (not shown) connected to the first connecting portion. wherein the first connecting portion is used for being matched with the hole structure to enable the two connecting couplers to be cooperatively connected, and the second connecting portion may swing relative to the first connecting portion. For example, the second connecting portion is a flexible structure, so that a certain adjusting space is formed between the two portions connected to each other.

The first mounting part 211 and/or the second mounting part 221 in the embodiments described above may be one of a variety of shapes, such as rectangular, circular, etc.

It should be noted that when the power connecting coupler of the power mechanism and the driven connecting coupler of the operating arm are movable along the abutting direction, it may use substantially the same structure as the connecting coupler of the connecting mechanism and its associated structure. For example, a power connecting coupler of a power mechanism is movable along the abutting direction. Specifically, the power mechanism has a power body and an elastic unit. The power body defines a power mounting slot. The power connecting coupler is received in the power mounting slot, and the edge area of the power connecting coupler abuts against the power body to limit the movement of the power connecting coupler. The elastic unit includes a first connecting post and a second connecting post elastically connected to the first connecting post. The first connecting post and the second connecting post abut against the bottom surfaces of the power connecting coupler and the power mounting slot respectively. In addition, the bottom surfaces of the power connecting coupler defines receiving holes for receiving the first connecting post and/or the second connecting post. The power connecting coupler may also extend out of the power mounting slot. As another example, the driven connecting coupler of the operating arm is movable along the abutting direction. Specifically, the operating arm includes a driving body and an elastic unit. The driving body defines a driven mounting slot. The driven connecting coupler is received in the driven mounting slot, and the edge area of the driven connecting coupler abuts against the driving body to limit the movement of the driven connecting coupler. The elastic unit includes a first connecting post and a second connecting post elastically connected to the first connecting post. The first connecting post and the second connecting post abut against the bottom surfaces of the driven connecting coupler and the driven mounting slot. In addition, the bottom surface of the driven connecting coupler and/or the drive mounting slot define a receiving hole for receiving the first connecting post and/or the second connecting post. In another embodiment, the driven connecting coupler may also extend out of the driven mounting slot.

In one embodiment, the connecting mechanism includes a first connecting coupler and a second connecting coupler. Wherein at least one of the first connecting coupler 210 and the power connecting coupler 202 is movable along a first direction relative to the body, and at least one of the second connecting coupler 220 and the driven connecting coupler 203 is movable along the second direction relative to the body, thereby adjusting the coaxiality of the power connecting coupler 202 and the driven connecting coupler 203. Wherein the first direction forms an included angle with the rotating shaft of the first connecting coupler, and the second direction forms an included angle with the rotating shaft of the second connecting coupler. Furthermore, the first connecting coupler and the second connecting coupler rotate synchronously. For example, the first connecting coupler 210 and the driven connecting coupler 203 is movable relative to the body in a direction perpendicular to the rotating shaft. As another example, the second connecting coupler 220 and the power connecting coupler 202 are capable of moving relative to the main body in a direction perpendicular to the rotating axis.

The connecting couplers are movable relative to the main body. The two connecting couplers, connected to each other, may move relative to each other or may be stationary relative to each other. In one embodiment, the first connecting coupler is movable relative to the main body, and at the moment, the power connecting coupler is movable relative to the first connecting coupler and moves with the first connecting coupler, and is also capable of moving relative to the first connecting coupler. For example, as shown in FIG. 10 and FIG. 11, the power connecting coupler slides along the first mounting part to adjust the coaxiality. In one embodiment, the first connecting coupler is stationary relative to the main body, and at this time, the power connecting coupler is movable relative to the body and the first connecting coupler. For example, the power connecting coupler is stationary relative to the power body and slides along the first mounting part to be movable relative to the main body and the first connecting coupler. As another example, the power connecting coupler is movable relative to the main body and is capable of sliding along the first mounting part.

When the connecting mechanism 10 with the connecting unit 200 is connected to the corresponding operating arm 23 and the power mechanism 22, at least one of the connecting couplers abutting against each other is movable relative to the main body, thereby adjusting the coaxiality between the driven connecting coupler 203 and the power connecting coupler 202, and enabling the operation and control of the operating arm 23 to more accurate and the service life to be prolonged.

It should be noted that the first connecting coupler 210 and the second connecting coupler 220 are movable independently or synchronously when the first connecting coupler and the second connecting coupler of the connecting mechanism are movable along the first direction and the second direction respectively relative to the main body. For example, the first connecting coupler 210 and the second connecting coupler 220 are slidably connected along an adjustment direction, thereby enabling the first connecting coupler 210 and the second connecting coupler 220 to be movable relative to each other. At this point, the first mounting part and the second mounting part may be tapered slots. In another embodiment, the first connecting coupler 210 and the second connecting coupler 220 are also movable synchronously, and at the moment, the connecting unit moves in the mounting slot to adjust the coaxiality between the first connecting coupler 210 and the second connecting coupler 220.

Figure 12:
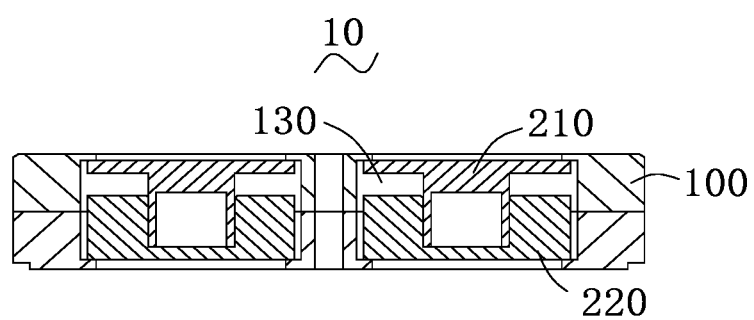
FIG. 12 is a structural schematic view of an embodiment of a connecting mechanism according to the present disclosure.
Figure 13:
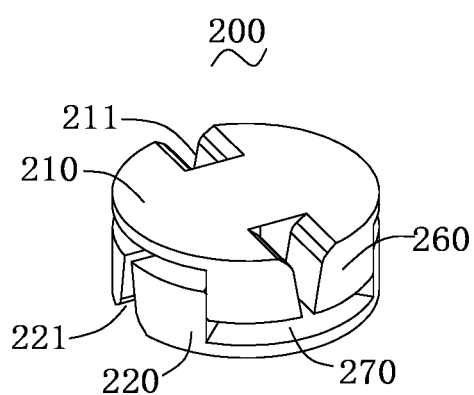
FIG. 13 is a structural schematic view of an embodiment of a connecting unit according to the present disclosure.
Figure 14:
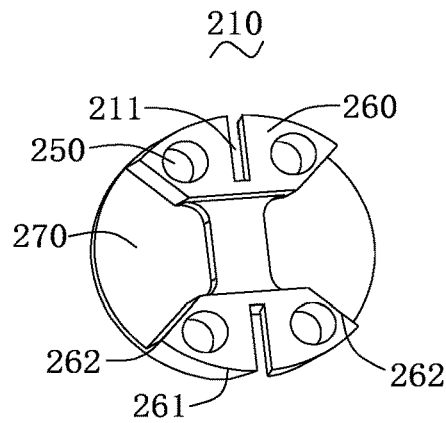
FIG. 14 is a structural schematic view of a first connecting coupler according to the present disclosure.

Please refer to FIGS. 12-14, in one embodiment, the first connecting coupler 210 and the second connecting coupler 220 is movable relative to the main body. Specifically, the first connecting coupler 210 is movable along a first direction limited by the first mounting part 211, and the second connecting coupler 220 is movable relative to the main body along a second direction limited by the second mounting part 221. The first direction and the second direction are perpendicular to the rotating shaft, and the two directions intersect with the projection on the first connecting coupler 210 or the second connecting coupler 220, i.e., the two directions are non-parallel.

As shown in FIG. 12, in one embodiment, the first connecting coupler 210 and the second connecting coupler 220 of the connecting unit are received in the mounting slot 130 of the main body and are movable in the mounting slot 130 along a direction perpendicular to the rotation axis of the main body. Specifically, a gap is formed between each connecting coupler and the side wall of the mounting slot, thereby the connecting coupler is movable in the mounting slot. For example, the first connecting coupler and the second connecting coupler is movable along a plane of a surface of the main body. At this point, the rotation axis of the first connecting coupler and the rotation axis of the second connecting coupler are both perpendicular to the plane. When the first connecting coupler 210 is connected to the power connecting coupler 202, the first connecting coupler 210 is movable freely in the plane, and when the connecting unit 200 is reconnected to the driven connecting coupler 203, the connecting unit 200 is only movable along the first direction and the second direction during the mounting process due to the limitation of the first mounting part 211 and the second mounting part 221.

In another embodiment, the mounting part may be at least part of the coupler area of the connecting coupler. At this point, the plurality of connecting couplers is capable of being magnetically connected to each other, and the coaxiality is adjusted through the gap between the connecting coupler and the main body.

The first connecting coupler and the second connecting coupler may also be stationary relative to the main body along the plane, that is, the two connecting couplers are stationary along the plane. At this point, the power connecting coupler and the driven connecting coupler are movable relative to the main body. In one embodiment, the first connecting coupler defines a first mounting part to enable the first connecting coupler and the power connecting coupler connected to the first connecting coupler to be movable in the first direction. The second connecting coupler defines a second mounting part to enable the second connecting coupler and the driven connecting coupler connected to the second connecting coupler to be movable in the second direction.

In the embodiment shown in FIG. 13, the first mounting part 211 and the second mounting part 221 are strip-shaped holes, wherein the first direction is the extending direction of the first mounting part, and the second direction is the extending direction of the second mounting part. At this point, the power connecting coupler 202 and the driven connecting coupler 203 have corresponding post structures, such as the mounting posts 214, so as to be correspondingly connected to the first mounting part and the second mounting part. The post structures are movable in the strip-shaped holes to adjust the coaxiality, that is, the first connecting coupler and the power connecting coupler are movable, and the second connecting coupler and the driven connecting coupler are movable relative to each other. In another embodiment, only one of the mounting parts is a strip-shaped hole. Alternatively, the two mounting parts may be another shape, such as a post structure. At this point, a corresponding strip-shaped hole is formed in the power connecting coupler and the driven connecting coupler.

It should be noted that, in another embodiment, the embodiments shown in FIG. 12 and FIG. 13 may also be combined. For example, the main body has a plurality of connecting units. At this point, the driven connecting coupler and the power connecting coupler move in the mounting part to adjust the coaxiality, and the gap between the connecting unit and the side wall of the mounting slot of the body is mainly used for adjusting the coaxiality when the driven connecting coupler and the power connecting coupler are connected to the plurality of connecting units, thereby enabling the plurality of connecting units to be connected to the corresponding connecting coupler. That is, the gap between the connecting unit and the mounting slot is capable of adjusting the coaxiality, and adjust the position between the connecting units, so that the plurality of connecting units are correspondingly connected to the corresponding driven connecting coupler and the power connecting coupler.

In one embodiment, the first mounting part 211 and the second mounting part 221 passes through the side surfaces of the of the first connecting coupler 210 or the second connecting coupler 220 of the mounting part to facilitate processing. In another embodiment, only the first mounting part passes through the side surface of the first connecting coupler, or only the second mounting part passes through the side surface of the second connecting coupler 220. Alternatively, the two mounting parts may not pass through the side surfaces of the connecting couplers.

In addition, in one embodiment, the first mounting part 211 and the second mounting part 221 are tapered holes, so that the mounting gap between the plurality of connecting couplers is further reduced, thereby enabling the first mounting part, the second mounting part and the power connecting coupler to be connected more tightly. In another embodiment, the two mounting parts may also be non-tapered holes, or only the first mounting part or the second mounting part may be a tapered hole.

In one embodiment, the first connecting coupler 210 and the second connecting coupler 220 are arranged opposite to each other. The first mounting part 211 and the second mounting part 221 are respectively located on the surfaces of the first connecting coupler 210 and the second connecting coupler 220 opposite to each other. There are two first mounting parts 211 and the two first mounting parts 211 are arranged along the first direction. There are two second mounting parts 221 and the two second mounting parts 221 are arranged along the second direction. In another embodiment, the first direction and the second direction may be other directions as well. For example, the first direction is a direction perpendicular to the arrangement direction of the plurality of first mounting parts 211, and the second direction is a direction perpendicular to the arrangement direction of the plurality of second mounting parts 221.

In one embodiment, the intersection point of the first direction and the second direction on the first connecting coupler 210 or the second connecting coupler 220 is located on the first connecting coupler 210 or the second connecting coupler 220. For example, the intersection point is located in the central area of the first connecting coupler 210 and/or the second connecting coupler 220. As another example, the first connecting coupler 210 and the second connecting coupler 220 are central symmetry structures, and the intersection point is located in the symmetric center of the first connecting coupler 210 and/or the second connecting coupler 220. In another embodiment, the intersection point may also be located out of the first connecting coupler 210 or the second connecting coupler 220.

In one embodiment, the first direction is non-parallel to the second direction. For example, the first direction is orthogonal to the second direction. As another example, the first direction forms an acute angle with the second direction. In another embodiment, the first direction may also be the same as the second direction.

In one embodiment, the first direction is perpendicular to the rotation axis of the first connecting coupler, and/or the second direction is perpendicular to the rotation axis of the second connecting coupler. That is, a connecting coupler, movable relative to the main body, is movable in a vertical direction with the rotation axis of the connecting coupler. In another embodiment, the first direction may also form an acute angle with the first connecting coupler, and the second direction may also form an acute angle with the second connecting coupler. It should be noted that the first direction and the second direction are both non-abutting directions.

Referring to FIG. 14, in one embodiment, the first connecting coupler 210 and the second connecting coupler 220 are connected to each other. Specifically, each of the first connecting coupler 210 and the second connecting coupler 220 includes protrusions 260. There are two protrusions 260 located on the first connecting coupler 210 and/or the second connecting coupler 220 and arranged at intervals. A recessed area 270 is formed between the two adjacent protrusions 260. The protrusion 260 of the first connecting coupler 210 is received in the recessed area 270 of the second connecting coupler 220, and abuts against the two adjacent protrusions 260 of the second connecting coupler 220; and/or the protrusion 260 of the second connecting coupler 220 is received in the recessed area 270 of the first connecting coupler 210, and abuts against the two adjacent protrusions 260 of the first connecting coupler 210. It should be noted that in one embodiment, when the first connecting coupler and/or the second connecting coupler define receiving holes 250, and the receiving holes are formed in the protrusions.

In the present embodiment, each of the first connecting coupler 210 and the second connecting coupler 220 has two protrusions 260 and two recessed areas 270. For example, two protrusions are arranged opposite to each other. The two protrusions 260 of the first connecting coupler 210 are received in the two corresponding recessed areas 270 of the second connecting coupler 220 respectively, and the two protrusions 260 of the second connecting coupler 220 are received in the two corresponding recessed areas 270 of the first connecting coupler 210. The first mounting part and the second mounting part are located in regions of protrusions of the connecting coupler. In another embodiment, the number of the protrusions 260 and the recessed areas 270 may be different. For example, the first connecting coupler 210 has two protrusions 260 and a recessed area 270, and the second connecting coupler 220 has one protrusion 260 to be received in the recessed area 270 of the first connecting coupler 210. It should be noted that when the connecting coupler has one protrusion 260, the mounting part is located in a region of the protrusion 260 of the connecting coupler.

In addition, the recessed area 270 of the receiving protrusion 260 is matched with the protrusion 260, thereby enabling the first connecting coupler 210 and the second connecting coupler 220 to be engaged with each other. That is, the protrusion 260 of the first connecting coupler 210 is matched with the corresponding recessed area 270 of the second connecting coupler 220, and the recessed area 270 of the first connecting coupler 210 is matched with the corresponding protrusion 260 of the second connecting coupler 220. When there is a plurality of protrusion 260, at least one protrusion 260 matches the corresponding recessed area 270. In this way, the first connecting coupler 210 and the second connecting coupler 220 may be connected to each other without other connectors.

In one embodiment, the protrusion 260 has a first side surface 261 and two second side surface 262 adjacent to the first side surface 261, wherein the first side surface 261 of the protrusion 260 of the first connecting coupler 210 is adjacent to the peripheral edge of the first connecting coupler 210 and extends along the periphery edge. The first side surface 261 is aligned with the corresponding area of the periphery edge of the first connecting coupler 210. In the present embodiment, the first connecting coupler is a circular coupler, at this point, the first side surface is an arc surface. In another embodiment, the connecting coupler may be another shape, such as a rectangle or the like. The two second side surfaces 262 are located on the same side of the first side surface 261, and the two second side surfaces 262 or the planes on which the two second side surfaces 262 are located form an included angle and the included angle is non-zero degrees or 360 degrees, i.e., the two second side surfaces 262 are not arranged in the same plane. It should be noted that in another embodiment, the two second side surfaces may also be located on both sides of the first side surface. In the present embodiment, the protrusion 260 of the second connecting coupler 220 is the same as the one of the first connecting coupler 210, and it is not repeated here. In another embodiment, the protrusion 260 of the second connecting coupler 220 and the first connecting coupler 210 may also be structurally distinct.

In addition, the two opposite second side surfaces 262 of the two protrusions 260 of the first connecting coupler for forming the recessed area 270 abut against the two second side surfaces 262 of the protrusions 260 of the second connecting coupler, thereby enabling the two connecting couplers to be engaged with each other. That is, the second side surfaces 262 of the two connecting couplers correspondingly abut against each other.

In one embodiment, the protrusions 260 and the recessed areas 270 of the first connecting coupler 210 and/or the second connecting coupler 220 are arranged in a circle. For example, there are two protrusions 260 of each of the first connecting coupler 210 and the second connecting coupler 220 and the two protrusions 260 are oppositely arranged. The protrusions 260 and the recessed areas 270 of the connecting couplers are arranged in a circle, thereby enabling the two connecting couplers to be engaged with each other more accurately. Further, the moving position is more accurate when the connecting coupler moves by the mounting part of the connecting coupler, and the coaxiality of the operating arm 23 and the power mechanism is improved. In another embodiment, the protrusion 260 of the connecting coupler may also be a center-to-center symmetric structure. For example, the connecting coupler is a center-to-center symmetric structure.

In one embodiment, the first connecting coupler 210 is the same as the second connecting coupler 220. When the two connecting couplers are engaged with each other, one protrusion 260 of one of the connecting couplers is received in the recessed area 270 of the other connecting coupler, and the first direction limited by the first mounting part 211 forms an included angle with the second direction limited by the second mounting part 221. Thus, not only the structure of the connecting mechanism 10 is simplified, but also the production efficiency is improved.

It should be noted that in another embodiment, the first connecting coupler 210 and the second connecting coupler 220 may not be connected to each other by the engagement of the recessed area 270 and protrusion 260. For example, the first connecting coupler 210 and the second connecting coupler 220 are connected to each other by threaded fasteners. At this point, the two connecting couplers may still have the protrusions 260, and the protrusions 260 of the two connecting couplers abut against each other for positioning the two connecting couplers. As another example, the connecting coupler has an engaging structure to engage with the two connecting couplers.

It should be noted that the power connecting coupler of the power mechanism is movable relative to the main body in the first direction, and the driven connecting coupler of the operating arm is movable relative to the main body in the second direction, the power connecting coupler and the driven connecting coupler may be substantially the same structure as the connecting coupler of the connecting mechanism.

For example, a power connecting coupler of a power mechanism is movable relative to the main body in a first direction. Specifically, the power mechanism has a power body. The power body abuts against the main body of the connecting mechanism, and the power connecting coupler is arranged on the power body. The power connecting coupler has a first mounting part. The power connecting coupler is movable relative to the power body in a first direction limited by the first mounting part; and/or the power connecting coupler is relatively movable in a first direction limited by the first mounting part. Furthermore, the power connecting coupler includes two first mounting parts, and the first direction is the arrangement direction of the first mounting part. Alternatively, the first mounting part is a strip-shaped hole, and the extending direction of the first mounting part is the first direction. In one embodiment, the first mounting part is a hole structure and passes through the side surface of the periphery edge of the power connecting coupler. In one embodiment, the first direction is perpendicular to the rotation axis of the power connecting coupler.

As another example, the driven connecting coupler of the operating arm is movable relative to the main body in a second direction. Specifically, the operating arm includes a driving body. The driving body abuts against the main body of the connecting mechanism. The driven connecting coupler is arranged on the driving body. The driven connecting coupler has a second mounting part. The driven connecting coupler is movable relative to the driving body in a second direction limited by the second mounting part; and/or the second connecting coupler is relatively movable in the second direction limited by the second mounting part. In addition, the driven connecting coupler includes two second mounting parts, and the second direction is the arrangement direction of the second mounting part. Alternatively, the second mounting part is a strip-shaped hole, and the extending direction of the second mounting part is the second direction. In one embodiment, the second mounting part is a hole structure, and the side surface of the periphery edge of the driven connecting coupler has the mounting part. In one embodiment, the second direction is perpendicular to the rotation axis of the driven connecting coupler.

The embodiments described above introduce a specific scheme for adjusting the coaxiality and mounting gaps when the connecting mechanism is connected to the operating arm and the power mechanism. It should be noted that, in another embodiment, when the connecting mechanism, the operating arm, and the power mechanism are connected, at least one of the connecting mechanism, the operating arm, and the power mechanism is capable of adjusting the coaxiality and the mounting gaps. For example, the first connecting coupler and/or the second connecting coupler is capable of moving along the abutting direction and moving along the first direction and/or the second direction relative to the main body. As another example, the first connecting coupler is capable of moving along the abutting direction, and the second connecting coupler is capable of moving along the second direction relative to the main body. Alternatively, the second connecting coupler is capable of moving along the abutting direction, and the first connecting coupler is capable of moving along the first direction relative to the main body. As another example, the first connecting coupler and the second connecting coupler are both movable along the abutting direction and are capable of moving relative to the main body along a direction perpendicular to the rotation axis. As another example, the first connecting coupler and/or the power connecting coupler is capable of moving along the abutting direction and is capable of moving relative to the body along a direction perpendicular to the rotating axis. The second connecting coupler and/or the driven connecting coupler is capable of moving along the abutting direction and moving relative to the main body along a direction perpendicular to the rotating axis.

At this point, the first connecting coupler and the second connecting coupler is capable of moving independently or synchronously in the moving direction of the first connecting coupler. For example, the first connecting coupler and the second connecting coupler move independently in the abutting direction and move synchronously in a direction perpendicular to the rotation axis. As another example, the first connecting coupler and the second connecting coupler move independently in a direction perpendicular to the rotation axis.

It should be noted that the structure of each connecting coupler is the same as the connecting coupler in the embodiments described above and the structure associated therewith, and is not repeated here.

Figure 15:
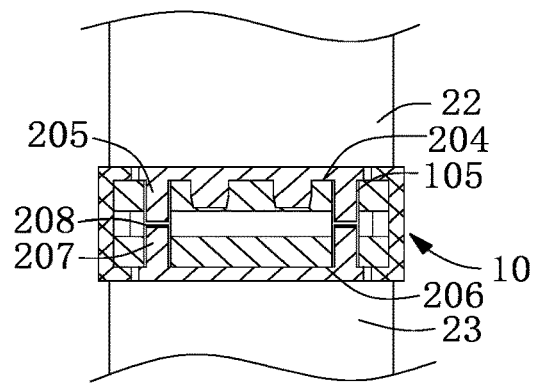
FIGS. 15 to 19 are structural schematic views of different embodiments of a slave operating device according to the present disclosure.

Referring to FIG. 15, the slave operating device 2 includes a connecting mechanism 10, an operating arm 23 and a power mechanism 22, wherein the connecting mechanism 10 defines a through hole 150. The power mechanism 22 has a first connecting surface 204, abutting against the connecting mechanism 10. A first detecting portion 205 is disposed on the first connecting surface 204. The operating arm 23 has a second connecting surface 206 abutting against the connecting mechanism 10. A second detecting portion 207 is disposed on the second connecting surface 206. The first detecting portion 205 and/or the second detecting portion 207 are received in the through hole 150. The first detecting portion 205 or the second detecting portion 207 has a sensor 208 for detecting the distance between the first detecting portion 205 and the second detecting portion 207, thereby obtaining an abutting state between the first and second connecting surfaces 204, 206 and the connecting mechanism. The power connecting coupler is disposed on the first connecting surface 204, and the driven connecting coupler is disposed on the second connecting coupler.

When the operating arm 23 and the power mechanism 22 are connected to the connecting mechanism, the first connecting surface 204 abuts against the first mounting wall and the second connecting surface 206 abuts against the second mounting wall if the distance between the first detecting portion 205 and the second detecting portion 207 detected by the sensor 208 is within a preset range. At this time, the sensor 208 sends out the abutting information for subsequent operation. If the first connecting surface 204 and/or the second connecting surface 206 do not abut against the corresponding mounting wall of the connecting mechanism, the distance detected by the sensor 208 is outside the preset range, and the sensor 208 is not triggered to send out the abutting information.

The slave operating device, having the operating arm 23 and the power mechanism 22, is capable of detecting the connecting state between the first and second connecting surfaces 204, 206 and the power mechanism 22 by the sensor 208 passing through the through hole 150. Each connecting surface does not need a sensor to be disposed thereon for detecting the abutting state between the first connecting surface 204 and the first mounting wall, or between the second connecting surface 206 and the second mounting wall. In this way, not only the design is simplified, but also the production efficiency and stability are further improved.

In one embodiment, the first detecting portion 205 and the second detecting portion 207 are received in the through hole 150. Specifically, the first detecting portion 205 and the second detecting portion 207 are post structures, and the end surface of the free ends of the first detecting portion 205 and the second detecting portion 207 are oppositely arranged and are received in the through holes 150. Wherein the free end refers to the end part for connecting to the connecting sensor 208 or being close to the connecting sensor 208. In this case, the sensor 208 is located in the through hole 150.

In another embodiment, the first detecting portion 205 passes through the through hole 150, and the second detecting portion 207 is a slot structure. Specifically, the free end of the first detecting portion 205 extends out of the through hole 150 or is located in the through hole 150 and adjacent to the edge area of the through hole 150. The sensor 208 is disposed on the first detecting portion 205 and extends out of or located in the through hole 150 for detecting the distance from the bottom surface of the slot structure. Or the sensor 208 is disposed on the bottom surface of the slot structure for detecting the distance from the first detecting portion 205. The second detecting portion 207 may also pass through the through hole 150, and the first detecting portion 205 is a slot structure. At this point the structures is similar to the embodiments described above and is not repeated here.

In one embodiment, there is a plurality of the first detecting portion 205. The through holes 150, the second detecting portion 207, and the sensor 208 are oppositely arranged. For example, the number of the first detecting sections 205 and the number of the second detecting sections 207 are both three, and the first detecting sections 205 and the second detecting sections 207 are both arranged in a triangular. The first detecting portion 205 and/or the second detecting portion 207 are arranged in a triangular, and the first detecting portion 205 and/or the second detecting portion 207 are arranged in a triangular shape. The first detecting portion 205 and/or the second detecting portion 207 pass through the through hole 150, the length of the first detecting portion 205 may be different, that is, the end surface of the free end of the plurality of first detecting portions 205 is different from the distance of the first connecting surface 204, and the second detecting portion 207 corresponds to the arrangement. For example, one of the first detecting portions 205 is located in the through hole 150, and a first detecting portion 205 extends out of the through hole 150.

In one embodiment, the first detecting portion 205 and/or the second detecting portion 207 are matched with the through hole 150 during installation, and at this point, the positioning hole can be replaced with the through hole 150.

In one embodiment, the sensor 208 is a distance sensor 208 and/or a pressure sensor 208. For example, there is a plurality of sensors 208, and the plurality of sensor 208 is distance sensors. and when the abutting information fed back by the plurality of sensors 208 is within a preset range, the operating arm 23, the power mechanism 22, and the connecting mechanism reach a connecting requirement for subsequent operation. As another example, a part of the plurality of sensors 208 may be pressure sensors 208 and the other part of the plurality of sensors 208 are distance sensors 208. The operating arm 23, the power mechanism 22, and the connecting mechanism reach a connecting requirement when the abutting information fed back by the pressure sensors 208 and the distance sensors 208 is within a preset range. As another example, the sensors 208 is capable of detecting not only the pressure information but also the distance information.

Figure 16:
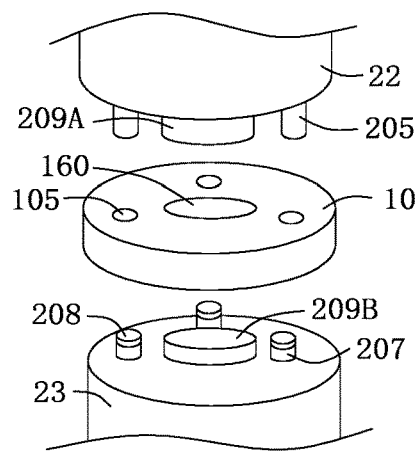

Referring to FIG. 16, in one embodiment, an electromagnet assembly 209 is located between the power mechanism 22 and the operating arm 23. The electromagnet assembly 209 is used for connecting to the connecting mechanism and the operating arm 23 according to the abutting information fed back by the sensor 208. When the feedback information is within the preset range, the electromagnet assembly is triggered to connect to the power mechanism 22, the connecting mechanism, and the operating arm 23.

Specifically, in one embodiment, the electromagnet assembly includes a magnetic portion 209a, an absorbing portion 209b. The absorbing portion 209b is made of a material capable of being absorbed by the magnetic portion. The magnetic portion 209a is disposed on the first connecting surface 204 or the second connecting surface 206, and the magnetic portion 209a and the absorbing portion 209b pass through the connecting mechanism 10 and are connected to each other. For example, the connecting mechanism defines a receiving hole 160, and the magnetic portion 209a and the absorbing portion 209b are both received in the receiving hole 160, i.e., the magnetic portion and the absorbing portion are magnetically connected in the receiving hole 160. As another example, the magnetic portion is disposed on the first connecting surface 204 and passes through the receiving hole 160, and the absorbing portion is disposed on the second connecting surface 206 and is in the same plane with the second connecting surface 206.

In another embodiment, the power mechanism 22, the operating arm 23, and the connecting mechanism are provided with an electromagnet assembly for connecting the power mechanism 22, the connecting mechanism and the operating arm 23 according to the information fed back by the sensor 208. Specifically, the electromagnet assembly includes a magnetic portion and an absorbing portion, wherein the magnetic portion is disposed on the connecting mechanism, and there is a plurality of absorbing portions disposed on the first connecting surface 204 and the second connecting surface 206 respectively, thereby enabling the operating arm 23, the connecting mechanism and the power mechanism to be magnetically connected. For example, the connecting mechanism defines a receiving hole 160, and the magnetic portion is received in the receiving hole 160. The two surfaces of the magnetic portion, facing the first connecting surface 204 and the second connecting surface 206, are magnetically connected to the absorbing portions on the first connecting surface 204 and the second connecting surface 206 respectively, thereby enabling the operating arm 23, the power mechanism 22 and the connecting mechanism are connected to each other.

In one embodiment, there is a plurality of sensors 208 and the sensors 208 are placed around the electromagnet assembly. For example, the magnetic portion is disposed in the middle area of the connecting mechanism, and the absorbing portions are disposed on the first connecting surface 204 and the second connecting surface 206. The first detecting portion 205 is disposed on the first connecting surface 204 surrounding the absorbing portion, and the sensors 208 are disposed on the first detecting portion 205.

It should be noted that, in each of the above embodiments, the sensors 208 is capable of detecting the abutting state of the connecting surface, and the electromagnet assembly can be used to connect to the power mechanism 22, the connecting mechanism and the operating arm 23.

Figure 17:
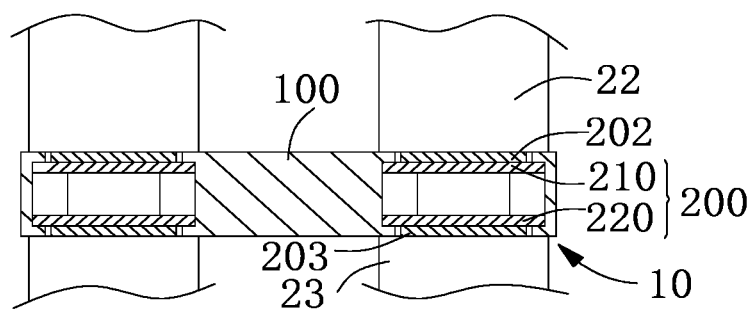
Figure 18:
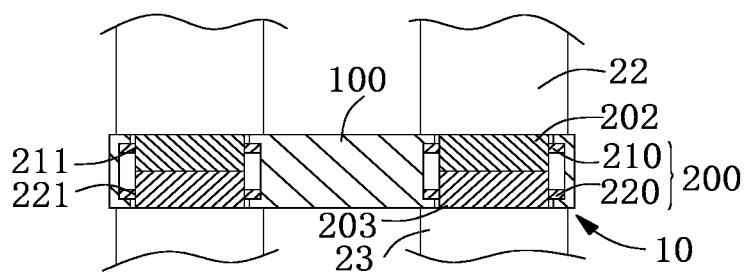
Figure 19:
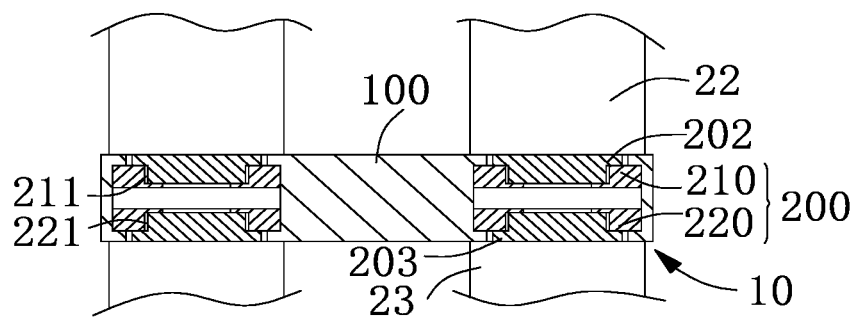

As shown in FIGS. 17-19, the plurality of connecting couplers may also be connected by other means.

In one embodiment, the slave operating device 2 includes a connecting mechanism 10, a power mechanism 22, and an operating arm 23. Specifically, the power mechanism 22 has a power connecting coupler 202. The connecting mechanism 10 has a main body 100 and a connecting unit 200 disposed on the main body 100. The connecting unit 200 has a first connecting coupler 210 and a second connecting coupler 220. The power connecting coupler 202 is connected to the first connecting coupler 210, the driven connecting coupler 203 is connected to the second connecting coupler 220, and the power connecting coupler 202 is magnetically connected to the driven connecting coupler 203, thereby enabling the power connecting coupler to drive the driven connecting coupler 203 to further drive the operating arm 23 to perform the required operation.

It should be noted that the power connecting coupler 202 is rotatable to drive the driven connecting coupler 203. At this point, the connecting unit 200 is capable of rotating relative to the main body 100. The power connecting coupler 202 is capable of driving the driven connecting coupler 203 along a straight line, and the connecting unit 200 is capable of moving relative to the main body 100 in the driving direction. Each connecting coupler and connecting unit 200 are also capable of moving in the abutting direction and/or in a first direction/second direction. For example, the first connecting coupler 210 and the second connecting coupler 220 are capable of moving relative to each other to reduce the mounting gap.

The power connecting coupler 202 is magnetically connected to the driven connecting coupler 203. The power connecting coupler 202 is directly and magnetically connected to the driven connecting coupler 203, or the power connecting coupler 202 is magnetically connected to the driven connecting coupler 203 via the connecting unit 200. Specifically, at least one of the driven connecting coupler 203, the power connecting coupler 202 and the connecting unit 200 has magnetism to enable the power connecting coupler 202 to drive the driven connecting coupler 203.

As shown in FIG. 17, in one embodiment, the power connecting coupler 202 is magnetically connected to the driven connecting coupler 203 via the connecting unit 200. The connecting unit 200 is magnetic. The first connecting coupler 210 and the second connecting coupler 220 are magnetically connected to the power connecting coupler 202 and the driven connecting coupler 203 respectively. In another embodiment, the connecting coupler 203 is magnetic and is magnetically connected to the second connecting coupler 220. Alternatively, the power connecting coupler 202 is magnetic and is magnetically connected to the first connecting coupler 210.

In one embodiment, the first connecting coupler 210 is communicated with the second connecting coupler 220, and at the moment, the driven connecting coupler 203 and the power connecting coupler 202 abut against each other or are adjacent to each other through the communicating area, for magnetically connecting to each other. As shown in FIG. 18, the driven connecting coupler 203 passes through the second connecting coupler 220 to extend out of the second connecting coupler 220 and is magnetically connected to the power connecting coupler 202. The power connecting coupler 202 passes through the first connecting coupler 210 and is connected to the driven connecting coupler 203 within the connecting unit 200. In another embodiment, the power connecting coupler 202 may not pass through the first connecting coupler 210, at which point the driven connecting coupler 203 sequentially passes through the second connecting coupler 220 and the first connecting coupler 210 to be connected to the power connecting coupler 202. In another embodiment, the power connecting coupler 202 passes through the first connecting coupler 210 to extend out of the first connecting coupler 210 and is magnetically connected to the driven connecting coupler 203. Similarly, at this time, the driven connecting coupler 203 may or may not pass through the second connecting coupler 220. The power connecting coupler 202 passes through the first connecting coupler 210, and the driven connecting coupler 203 passes through the second connecting coupler 220. The power connecting coupler 202 and the driven connecting coupler 203 are arranged adjacent to each other for magnetically connecting to each other.

In one embodiment, the first connecting coupler 210 defines a first mounting part, and the second connecting coupler 220 defines a second mounting part in communication with the first mounting part. The power connecting coupler 202 is mounted in the first connecting coupler 210, the driven connecting coupler 203 is mounted in the second connecting coupler 220. The power connecting coupler 202 and the driven connecting coupler 203 abut against each other or are adjacent to each other via the first mounting part and the second mounting part communicated with the first mounting part, for magnetically connecting to each other. It should be noted that, in another embodiment, the two mounting parts may be not communicated with each other as long as it is ensured that the power connecting coupler 202 is magnetically connected to the driven connecting coupler 203.

In one embodiment, the first mounting part is located in a middle area of the first connecting coupler 210, and the second mounting part is located in a middle area of the second connecting coupler 220, wherein there is one or more first mounting parts. When there is a plurality of first mounting parts, the plurality of mounting parts may also be distributed along the peripheral edge of the connecting coupler.

In one embodiment, the first mounting part 211 and the second mounting part 221 are both hole structures. The power connecting coupler 202 is received in the first mounting part 211, and the driven connecting coupler 203 is received in the second mounting part 221. Wherein the bottom surfaces of the two mounting parts are communicated with each other, and the power connecting coupler 202 and the driven connecting coupler 203 abut against each other or are adjacent to each other through the communication area, for magnetically connecting to each other. For example, in the embodiment shown in FIG. 18, the bottom surfaces of the two mounting parts are all communicated with each other, that is, the bottom surfaces of the two mounting parts are in fully communicated with each other, and the power connecting coupler 202 and the driven connecting coupler 203 abut against each other through the communicating area. As another example, in the embodiment shown in FIG. 19, at least one partial area of the bottom surface of one mounting part is communicated with the bottom surface of another mounting part. In the embodiment, the power connecting coupler 202 is disposed adjacent to the driven connecting coupler 203 and is magnetically connected to the driven connecting coupler 203. In another embodiment, the power connecting coupler and the driven connecting coupler may also abut against each other by the communication area.

In addition, the two mounting parts are tapered holes, and the axes of the two tapered holes overlap. In another embodiment, the axes of the two mounting parts may not overlap, so long as the two mounting parts are communicated with each other.

In one embodiment, when the power connecting coupler 202 is magnetically connected to the driven connecting coupler 203 through the connecting unit 200, one of the power connecting couplers 202 and the first connecting coupler 210 defines a slot, and the end of the other one of the power connecting couplers 202 and the first connecting coupler 210 is received in the slot. And/or one of the second connecting coupler 220 and the driven connecting coupler 203 defines a slot, and the end of the other one of the second connecting coupler 220 and the driven connecting coupler 203 is received in the slot. In one embodiment, when the power connecting coupler 202 directly abuts against and is magnetically connected to the driven connecting coupler 203, one of the power connecting coupler 202 and the driven connecting coupler 203 defines a slot, and the end of the other one of the power connecting coupler 202 and the driven connecting coupler 203 is received in the slot.

In one embodiment, the first connecting coupler 210 and/or the power connecting coupler 202 define positioning units, and the second connecting coupler 220 and/or the driven connecting coupler 203 define positioning units. The positioning units are used for positioning the connecting couplers during installation. For example, the positioning unit is located at a peripheral edge of the connecting coupler. Specifically, the positioning units of the first connecting coupler 210 and the power connecting coupler 202 are distributed along the periphery edge of the first connecting coupler 210 and the power connecting coupler 202 respectively, and the positioning units of the second connecting coupler 220 and the driven connecting coupler 203 are respectively distributed along the periphery edge of the second connecting coupler 220 and the driven connecting coupler 203. The positioning units are protrusion structures and corresponding recess structures. The positioning unit may be a ring-shaped positioning unit continuously distributed along the periphery edge of the connecting coupler, or there is a plurality of positioning units distributed along the periphery edge of the connecting coupler. As another example, the first connecting coupler 210 and the second connecting coupler 220 define positioning units. The positioning units are used for receiving the power connecting coupler 202 and the driven connecting coupler 202. At this time, the power connecting coupler 202 and the driven connecting coupler 203 are received in the recessed structures or in the area limited by the protruding structures. In another embodiment, only the first connecting coupler 210, the power connecting coupler 202 may have positioning units therebetween, or only the second connecting coupler 220 and the driven connecting coupler 203 may have positioning units therebetween. It should be noted that if the power connecting coupler 202 directly abuts against the driven connecting coupler 203, the power connecting coupler 202 and/or the driven connecting coupler 203 defines positioning units.

In one embodiment, at least one of the power connecting coupler 202, the driven connecting coupler 203, and the connecting mechanism 10 has an electromagnet structure. For example, the power connecting coupler 202 has an electromagnet structure, the driven connecting coupler 203 and the connecting mechanism 10 are capable of being absorbed by a magnet, and at the moment, the power connecting coupler 202 passes through the connecting mechanism 10 and is magnetically connected to the driven connecting coupler 203. In addition, at least one of the power mechanism 22, the operating arm 23 and the connecting mechanism 10 has a sensor to trigger the electromagnet structure of the power connecting coupler 202, thereby enabling the power mechanism 22, the operating arm 23 and the connecting mechanism 10 to be connected together.

The various technical features of the above-described embodiments may be combined in any combination, so that the description is concise, and all possible combinations of the various technical features in the above-described embodiments are described. However, as long as the combination of these technical features does not conflict, it is to be understood that the scope of the present specification is not to be taken in a limiting sense.

The above-described embodiments have only expressed several embodiments of the present application, which are described in more detail and detail, but are not therefore to be construed as limiting the scope of the present application. It should be noted that variations and modifications may be made to one of ordinary skill in the art without departing from the spirit of the present application, all of which fall within the scope of the present application. Therefore, the scope of the appended claims should be accorded the broadest interpretation so as to encompass all such modifications and similar arrangements.

While the present disclosure has been described with reference to particular embodiments, the description is illustrative of the disclosure and is not to be construed as limiting the disclosure. Therefore, those of ordinary skill in the art can make various modifications to the embodiments without departing from the scope of the disclosure.

What is claimed is:

1. A connecting mechanism, comprising:
    a main body, comprising a first mounting wall and a second mounting wall configured for abutting against an operating arm and a power mechanism, respectively; and
    a connecting unit, disposed on the main body, the connecting unit comprising a first connecting coupler and a second connecting coupler, the first connecting coupler configured to abut against the power connecting coupler of the power mechanism along a first abutting direction, and the second connecting coupler configured to abut against the driven connecting coupler of the operating arm along a second abutting direction, wherein the power mechanism drives the operating arm by the connecting unit, at least one of the first connecting coupler and the power connecting coupler is movable along the first abutting direction, at least one of the second connecting coupler and the driven connecting coupler is movable along the second abutting direction;
    wherein the first connecting coupler comprises two protrusions arranged at intervals; two recesses region is formed between the two protrusions of the first connecting coupler, the second connecting coupler comprises two protrusions, two recesses regions are formed between the two protrusions of the second connecting coupler, each of the two protrusions of the second connecting coupler is received in one of the two recessed regions of the first connecting coupler, and abuts against the two protrusions of the first connecting coupler; each of the two protrusions of the first connecting coupler is received in one of the two recessed regions of the second connecting coupler, and abuts against the two protrusions of the second connecting coupler;
    wherein the first connecting coupler defines a first mounting part in which the first connecting coupler is movable along a first direction limited by the first mounting part relative to the main body, and/or the power connecting coupler is movable along the first direction relative to the first connecting coupler, the first direction is perpendicular to or forms an acute angle with a rotating shaft of the first connecting coupler;
    wherein the second connecting coupler defines a second mounting part in which the second connecting coupler is movable along a second direction limited by the second mounting part relative to the main body, and/or the driven connecting coupler is movable along the second direction relative to the second connecting coupler; the second direction is not parallel to the first direction, and the second direction forms an acute angle with a rotating shaft of the second connecting coupler.

2. The connecting mechanism of claim 1, wherein the first connecting coupler and the second connecting coupler are arranged opposite to each other.

3. The connecting mechanism of claim 2, wherein rotation axes of the first connecting coupler and the second connecting coupler of the connecting unit overlap.

4. The connecting mechanism of claim 1, wherein the first connecting coupler and the second connecting coupler of the connecting unit move independently relative to the main body.

5. The connecting mechanism of claim 1, wherein the main body defines a mounting slot, the connecting unit is received in the mounting slot, the mounting slot extends through the first mounting wall and the second mounting wall, and inner surfaces of the first mounting wall and the second mounting wall are configured to abut against edge areas of the first connecting coupler and the second connecting coupler, respectively, thereby limiting movements of the first mounting wall and the second mounting wall, respectively.

6. The connecting mechanism of claim 1, wherein the first connecting coupler is movable relative to the main body, and/or the second connecting coupler is movable relative to the main body.

7. The connecting mechanism of claim 6, wherein the connecting unit further comprises an elastic unit connected to the first connecting coupler and/or the second connecting coupler.

8. The connecting mechanism of claim 7, wherein each of two ends of the elastic unit abuts against the first connecting coupler and the second connecting coupler, respectively.

9. The connecting mechanism of claim 7, wherein the connecting unit further comprises a main body portion, and the first connecting coupler and the second connecting coupler are connected to the main body portion via the elastic unit.

10. The connecting mechanism of claim 7, wherein the elastic unit comprises a first connecting post and a second connecting post elastically connected to the first connecting post, and the first connecting post and the second connecting post abut against the first connecting coupler and the second connecting coupler, respectively.

11. The connecting mechanism of claim 7, wherein the first connecting coupler and/or the second connecting coupler defines a receiving hole, the first connecting post and/or the second connecting post is received in the receiving hole.

12. The connecting mechanism of claim 1, wherein the first mounting part and the second mounting part extend through a side surface of edge portion of the first connecting coupler or the second connecting coupler.

13. The connecting mechanism of claim 1, wherein an angle between rotation axes of the first connecting coupler and the second connecting coupler is an acute angle or a right angle.

14. The connecting mechanism of claim 1, wherein the recessed region of one of the first connecting coupler and the second connecting coupler receiving the protrusion of another one of the first connecting coupler and the second connecting coupler is configured to match with the protrusion, thereby the first connecting coupler is configured to be engaged with the second connecting coupler.

15. The connecting mechanism of claim 1, wherein a first side surface of each of the two protrusions of the first and the second connecting couplers is adjacent to a peripheral edge of the first connecting coupler and the second connecting coupler, respectively, and extends along the peripheral edge; the first side surface and the peripheral edge are coplanar; and an included angle between two side surfaces of each of the at least one protrusion adjacent to the first side surface is not 0 or 360 degrees.

16. The connecting mechanism of claim 1, wherein the first connecting coupler and the second connecting coupler have a same structure.

17. The connecting mechanism of claim 1, wherein the first direction is orthogonal to the second direction.

18. The connecting mechanism of claim 1, wherein the first direction forms an acute angle with the second direction.

* * * * *